United States Patent [19]

Sounik et al.

[11] Patent Number: 5,453,481
[45] Date of Patent: Sep. 26, 1995

[54] PROCESS FOR PREPARING VINYLPHENOL POLYMERS AND COPOLYMERS

[75] Inventors: James R. Sounik; Graham N. Mott; Charles B. Hilton, all of Corpus Christi, Tex.

[73] Assignee: Hoechst Celanese Corporation, Somerville, N.J.

[21] Appl. No.: 406,351

[22] Filed: Mar. 1, 1995

[51] Int. Cl.$^6$ .............................. C08G 8/02; C08G 65/38
[52] U.S. Cl. .................. 528/125; 528/212; 528/214; 528/215
[58] Field of Search ............................ 528/125, 212, 528/214, 215

[56] References Cited

U.S. PATENT DOCUMENTS

| Re. 34,122 | 11/1992 | Sheehan et al. | 525/241 |
|---|---|---|---|
| 4,032,513 | 6/1977 | Fujiwara et al. | 526/141 |
| 4,880,487 | 11/1989 | Sheehan et al. | 525/241 |
| 5,264,528 | 11/1993 | Sheehan et al. | 525/384 |
| 5,342,727 | 8/1994 | Vicari et al. | 430/157 |

*Primary Examiner*—Morton Foelak
*Attorney, Agent, or Firm*—James J. Mullen; Donald R. Cassady

[57] ABSTRACT

The present invention provides a unique and novel way of producing polyhydroxystyrene which comprises the steps of (a) heating 4-hydroxyacetophenone under suitable hydrogenation conditions of temperature and pressure in the presence of a suitable palladium catalyst and for a sufficient period of time to form 4-hydroxyphenylmethylcarbinol; (b) heating 4-hydroxyphenylmethylcarbinol under suitable conditions of temperature and pressure and for a sufficient period of time to form said polyhydroxystyrene.

21 Claims, No Drawings

5,453,481

PROCESS FOR PREPARING VINYLPHENOL POLYMERS AND COPOLYMERS

BACKGROUND OF THE INVENTION

1. Field of the Invention

The present invention relates to a process for the production of poly(4-hydroxystyrene) (PHS) directly from 4-hydroxyphenylmethylcarbinol (HPMC) which in turn is prepared from 4-hydroxyacetophenone (4-HAP).

2. Description of the Prior Art

It is known in the art to produce 4-hydroxystyrene (HSM) and derivatives thereof such as poly(4-hydroxystyrene) (PHS), which have applications in the production of adhesives, coating compositions, photoresists, and the like. In the PHS area, there is a need to produce such material in the least amount of process steps in order to provide efficiency. The prior art has utilized a five-step process in order to produce PHS. We have now found that PHS can be produced in three steps or less.

In the past, one of the ways of preparing poly(4-hydroxystyrene) (PHS) was the use of 4-hydroxystyrene (HSM) as the starting material; note European Patent Application No. 0-108-624. 4-Hydroxystyrene (HSM) is a well-known compound in the art.

Although there are several known ways to prepare 4-hydroxystyrene, these known methods are not commercially feasible in the further utilization of the 4-hydroxystyrene. The 4-hydroxystyrene itself is difficult to isolate, since it (1) readily decomposes, and (2) is toxic via skin absorption, and, as a result, those skilled in the art have made numerous attempts at finding a method of synthesizing PHS in a manner which avoids using the 4-hydroxystyrene as the starting material.

The following prior art references are disclosed in accordance with the terms of 37 CFR 1.56, 1.97, and 1.93.

U.S. Pat. No. 5,087,772 (issued Feb. 11, 1992) discloses the preparation of HSM by reacting 4-acetoxystyrene (ASM) with a suitable alcohol in the presence of a catalytic amount of a suitable base.

European Patent Application No. 0-128-984 (publication no.), filed Aug. 30, 1983, discloses a process for the production of para-vinyl phenol (HSM) by dehydrogenation of para-ethyl phenol.

European Patent Application No. 0-108-624 (publication no.), filed Nov. 4, 1983, discloses a process for the production of p-vinyl phenol polymer (polyhydroxystyrene polymer—PHS) by polymerizing p-vinyl phenol (HSM) in the presence of water and iron.

U.S. Pat. No. 4,032,513 (issued Jun. 28, 1977) discloses a process of producing PHS by cationically polymerizing HSM in the presence of a nitrile, such as $CH_3CN$, using a cationic polymerization initiator in a homogeneous reaction system.

U.S. Pat. No. 5,041,614 discloses a method for the preparation of 4-acetoxystyrene (ASM) from 4-acetoxyphenylmethylcarbinol. (Note Formula I for the structural formula for ASM).

U.S. Pat. No. 5,084,533 discloses a process for the neat hydrogenation of 4-acetoxyacetophenone in the production of 4-acetoxystyrene (ASM).

U.S. Pat. No. 5,151,546 discloses a process for preparing 4-acetoxystyrene (ASM) by heating 4-acetoxyphenylmethylcarbinol with an acid catalyst.

U.S. Pat. No. 5,245,074 discloses a process for preparing 4-acetoxystyrene (ASM) through the 4-acetoxyacetophenone/4-acetoxyphenylmethylcarbinol route.

U.S. Pat. No. 5,247,124 discloses a process for preparing substituted styrenes such as ASM by reacting a bisarylalkyl ether in the presence of an acid catalyst.

*J. Org. Chem.*, (1954), 19, 1205, discloses the use of copper chromite catalysts in the hydrogenation of ketones.

Other prior art references which relate to the present invention include U.S. Pat. No. 2,276,138; U.S. Pat. No. 3,547,858; U.S. Pat. No. 4,544,704; U.S. Pat. No. 4,678,843; U.S. Pat. No. 4,689,371; U.S. Pat. No. 4,822,862; U.S. Pat. No. 4,857,601; U.S. Pat. No. 4,868,256; U.S. Pat. No. 4,877,843; U.S. Pat. No. 4,898,916; U.S. Pat. No. 4,912,173; U.S. Pat. No. 4,962,147; and U.S. Pat. No. 4,965,400.

All of the above-cited prior art and any other references mentioned herein are incorporated herein by reference in their entirety.

SUMMARY OF THE INVENTION

The present invention provides a unique and novel way of producing vinyl phenol polymers such as p-vinyl phenol polymer [poly(4-hydroxystyrene) (PHS)]. Thus, there is provided a process for preparing polyhydroxystyrene which comprises the steps of (a) heating 4-hydroxyacetophenone (4-HAP) under suitable hydrogenation conditions of temperature and pressure in the presence of a suitable palladium catalyst and for a sufficient period of time to form 4-hydroxyphenylmethylcarbinol (HPMC) [sometimes referred to as 1-(4-hydroxyphenyl)ethanol-(1,4-HPE)]; (b) heating 4-hydroxyphenylmethylcarbinol under suitable conditions of temperature and pressure and for a sufficient period of time to form said polyhydroxystyrene (PHS).

DETAILED DESCRIPTION OF THE INVENTION

It has unexpectedly been found that PHS can be prepared directly by heating HPMC, with or without a diluent or solvent, for a sufficient period of time under suitable decomposition and polymerization conditions, after HPMC has been directly prepared by hydrogenating 4-HAP. In this manner, PHS can be prepared in a novel two-step process as compared to the five-step procedure of the prior art. Specifically, there is provided a process for preparing polyhydroxystyrene which comprises the steps of (a) heating 4-hydroxyacetophenone under suitable hydrogenation conditions of temperature and pressure in the presence of a suitable palladium catalyst and for a sufficient period of time to form 4-hydroxyphenylmethylcarbinol; and (b) heating 4-hydroxyphenylmethylcarbinol under suitable conditions of temperature and pressure and for a sufficient period of time to form said polyhydroxystyrene.

In the overall scheme of preparing PHS in a limited number of process steps, it has been unexpectedly found that the intermediate product, i.e. 4-hydroxymethylcarbinol (HPMC) can be efficiently prepared by hydrogenating 4-hydroxyacetophenone (4-HAP) under certain conditions. Specifically, it has been found that 4-HAP can be heated under suitable hydrogenation conditions of temperature and pressure in the presence of a suitable palladium catalyst and for a sufficient period of time to form HPMC in relatively high yields. The heating is conducted at a temperature of at least about 20° C., preferably from about 20° C. to about 100° C., in the presence of at least a stoichiometric amount of hydrogen and a catalyst selected from the group consisting of Pd/C; Pd/Al$_2$O$_3$; Pd/SiO$_2$; and Pd/CaCO$_3$.

In a preferred embodiment, the reaction is conducted until a substantial completion of hydrogenation is indicated by a lack of H$_2$ uptake, normally about one to twelve hours.

In a preferred embodiment, when Pd/C is used, the reaction proceeds at a pressure of from about 14.7 psig to about 5,000 psig, more preferably at a pressure of from about 50 psig to about 500 psig, and most preferably at a pressure of from about 100 psig to about 400 psig.

The hydrogenation conditions also include the use of a suitable solvent/diluent. Diluents/solvents which can be used in the present invention include: (a) water; (b) hydrocarbons such as benzene, toluene, xylene, and low-boiling point petroleum fractions; (c) inorganic gases such as carbon monoxide, carbon dioxide, nitrogen, helium, and argon; (d) dipolar aprotic solvents; (e) halogenated hydrocarbons such as chloroform, trichloroethane, or chlorobenzene, etc.; (f) carbon tetrachloride; and (g) mixtures thereof. The dipolar aprotic solvents employed are solvents which have a high dielectric constant and a high dipole moment but no acid hydrogen atoms; for example, such solvents include dimethylsulfoxide (DMSO), acetonitrile, dimethylformamide (DMF), dimethylacetamide, hexamethylphosphoric acid triamide (HMPT), and n-methyl pyrrolidone (NMP). Solvents such as ethanol, methanol, or tetrahydrofuran (THF) may be used in combination with the preceding solvents/diluents. Water, ethanol, methanol, benzene, and toluene (and mixtures thereof) are preferred diluents. The diluents are used in an amount of 2 to 200 mols, preferably 3 to 20 mols per mol of 4-HAP. It is to be understood that any diluent may be used under any temperature and reaction conditions so long as the hydrogenation of 4-HAP is effected smoothly.

The amount of catalyst employed is that which is catalytically effective in promoting the reaction. Usually, this amount is from about 0.001 weight percent to about 10.0 weight percent based on the weight of the starting material, i.e. 4-HAP.

The length of time which this heating/hydrogenation (reaction) step is conducted is not critical and the only requirement is that the heating be conducted for a period sufficient to form HPMC. Generally, this period is at least five minutes and may be as long as 25 hours, generally from about one to about twelve hours.

After the hydrogenation of 4-HAP, the end product (HPMC) is recovered from the reaction product and the residual fraction containing any unreacted 4-HAP can be recycled as the starting material for the next cycle of hydrogenation. The end product (HPMC) may be recovered from the reaction product by any method. One example is to recover the HPMC as a polymerized product, i.e. the reaction product is first subjected to a decomposition and a polymerization step [step (b) above] to polymerize the HPMC to the resulting polymer—polyhydroxystyrene (PHS).

In step (b) of the present invention, this consists of two phases, i.e. the first phase involves a decomposition of the carbinol in which a dehydration takes place and then the polymerization follows in a second phase. In this first phase, the decomposition takes place at the melting point of the carbinol being used as the starting material. Generally, such temperatures are at least 100° C., preferably from about 125° C. to about 300° C. Any pressure (atmospheric, sub-atmospheric, and/or super-atmospheric) can be used to facilitate this reaction. The reaction can be carried out with or without the use of a solvent (water or organic). The time required for phase one will vary depending, inter alia, upon the starting carbinol used and the temperature. The decomposition of the carbinol results in the formation of a monomer such as HSM.

In the second phase (the polymerization phase) of the monomer from phase one (step b) of the present invention thus is carried out at a reaction temperature of at least 70° C., preferably between 70°–300° C., and more preferably between 90°–200° C. The reaction pressure may be sub-atmospheric, atmospheric, or super-atmospheric.

The length of time which this heating (polymerization) phase is conducted is not critical and the only requirement is that the heating be conducted for a period sufficient to form PHS. Generally, this period is at least five minutes and may be as long as 25 hours.

Diluents/solvents which can be used in this second phase of step (b) of the present invention include: (a) water; (b) hydrocarbons such as benzene, toluene, xylene, and low-boiling point petroleum fractions; (c) inorganic gases such as carbon monoxide, carbon dioxide, nitrogen, helium, and argon; (d) dipolar aprotic solvents; (e) halogenated hydrocarbons such as chloroform, trichloroethane, or chlorobenzene, etc.; (f) carbon tetrachloride; and (g) mixtures thereof. The dipolar aprotic solvents employed are solvents which have a high dielectric constant and a high dipole moment but no acid hydrogen atoms; for example, such solvents include dimethylsulfoxide (DMSO), acetonitrile, dimethylformamide (DMF), dimethylacetamide, hexamethylphosphoric acid triamide (HMPT), and n-methyl pyrrolidone (NMP). Solvents such as ethanol, methanol, or tetrahydrofuran (THF) may be used in combination with the preceding solvents/diluents. Water, ethanol, methanol, benzene, and toluene (and mixtures thereof) are preferred diluents. The diluents are used in an amount of 2 to 200 mols, preferably 3 to 20 mols per mol of HPMC. It is to be understood that any diluent may be used under any temperature and reaction conditions so long as the polymerization of HSM is effected smoothly.

In carrying out the present invention, the amount of water, if present in the reaction system, is generally used in a range of 10% to 300% by weight, preferably 20% to 200% by weight, and more preferably, 50% to 100% by weight, based on the amount of the HPMC.

It is also within the scope of the present invention to employ polymerization inhibitors or accelerators in order to facilitate the reaction. Any substance may be used as the polymerization accelerator in the present invention if it accelerates or initiates polymerization of HPMC. For example, it is possible to use various polymerization accelerators described in Japanese Patent Publication (examined) Nos. 30123/82 and 47921/82 and Japanese Patent Publication (unexamined) Nos. 44607/82, 44608/82, and 44609/82, etc., all of which are incorporated herein by reference in their entirety.

Specific examples of the polymerization accelerators useful in the present invention include (1) cation initiators, e.g. (a) inorganic acids such as sulfuric acid, hydrochloric acid, nitric acid, or phosphoric acid, etc.; (b) metal halides such as aluminum chloride, tin tetrachloride, iron chloride, vanadium oxychloride, or boron trifluoride, etc.; (c) complexes such as ether complex of boron trifluoride or phenol complex of boron trifluoride, etc.; (d) aliphatic saturated monocarboxylic acids such as formic aid, bromacetic acid, idoacetic acid, trichloroacetic acid, oxyacetic acid, methoxyacetic acid, mercaptoacetic acid, cyanoacetic acid, propionic acid, 2-oxypropionic acid, n-butyric acid, isobutyric acid, n-valeric acid, isovaleric acid, 4-keto-n-valeric acid, methylethylacetic acid, trimethylacetic acid, caproic acid, heptoic acid, caprylic aid, pelargonic acid, or capric acid, etc.; (e) aliphatic saturated polycarboxylic acids such as oxalic acid, malonic acid, succinic acid, glutaric acid, adipic acid, pimelic acid, tartaric acid, polyacrylic acid, or citric acid, etc.; (f) aliphatic unsaturated monocarboxylic acids such as acrylic acid, crotonic acid, or methacrylic acid, etc.; (g) aliphatic unsaturated polycarboxylic acids such as maleic acid or fumaric acid, etc.; (h) aromatic carboxylic acids such as benzoic acid, hydroxybenzoic acid, methoxybenzoic acid, chlorobenzoic acid, bromobenzoic acid, iodobenzoic acid, cinnamic acid, salicylic acid, toluic acid, phthalic acid, isophthalic acid, terephthalic acid, trimellitic acid, or pyromellitic acid, etc.; or (i) organic sulfonic acids such as methanesulfonic acid; ethanesulfonic acid, benzenesulfonic acid, or toluenesulfonic acid, etc.; and (2) radical initiators, e.g. azoisobutyronitrile, benzoyl peroxide, or ammonium persulfate, etc.

Phenol complex of boron trifluoride, sulfuric acid, hydrochloric acid, oxalic acid, phosphoric acid, chloroacetic acid, bromoacetic acid, benzenesulfonic acid, and toluenesulfonic acid are preferred polymerization accelerators.

The amount of these polymerization accelerators used varies according to the kind thereof, reacting conditions to be adopted and desired molecular weight of the polymer, etc. However, the amount is generally preferred to be in the range of 0.005 to 10% by weight based on the amount of the HPMC.

It is also within the scope of the present invention processes to use a catalyst in order to further facilitate the polymerization reaction. Such catalysts include, without limitation, acids and bases such as $H_2SO_4$, $H_3PO_4$, NaOH, etc. The amount of catalyst employed is any amount which will facilitate (or catalytically effect) the reaction. Such amount will generally be from about 0.00001% by weight to about 2.0% by weight based on the total weight of HPMC employed.

After the polymerization of HSM, the end product (PHS) is recovered from the reaction product and the residual fraction containing any unreacted products can be recycled as the starting material for the next cycle. The end product (PHS) may be recovered from the reaction product by any method; for example, it can be separated from the fraction containing the unreacted products by filtration or any other suitable technique.

The following specific example is supplied for the purpose of better illustrating the invention. This example is not intended, however, to limit or restrict the scope of the invention in any way and should not be construed as providing conditions, parameters, or values which must be utilized exclusively in order to practice the present invention.

EXAMPLE I

Hydrogenation of 4-Hydroxyacetophenone

4-Hydroxyacetophenone (13.6 g, 0.1 mol) was charged in a 500 ml Zipper autoclave reactor, absolute alcohol (100 ml), and 5% Pd/C (Johnson Matthey's 21R) (1.2 g) was added. The autoclave was first checked for leaks with 100 psig of nitrogen. The autoclave was later pressurized to 300 psig with hydrogen and stirred at 35° C. for three hours. During this time, 0.095 mole of hydrogen was consumed (95% of the theoretical value). The reaction was vented and the contents filtered through a millipore filter yielding a colorless solution. Concentration of this solution in vacuo gave a solid. Traces of ethanol were removed via azeotropic distillation with toluene to afford a white solid (13.8 g). Liquid chromatographic analysis of the product showed 1,4-HPE (or HPMC) (99.0%), 4-HAP (0.2%), and 4-EP (ethyl phenol) (0.8%). $^1$H NMR spectrum of the product showed it to be mainly 1,4-HPE, with traces of 4-HAP.

EXAMPLES II–XII

Using the same procedure set forth in Example I, Examples II–XII were carried out using different reaction conditions as outlined in Table 1. The results are shown in Table 1.

TABLE 1

| | ANALYTICAL | | | | REACTION CONDITIONS | | | | | |
|---|---|---|---|---|---|---|---|---|---|---|
| Example No. | ex. std HPMC | 4-HAP | HSM | EP | RUN TIME | 4-HAP (g.) | CATALYST TYPE & AMOUNT | SOLVENT/ AMOUNT | $H_2$ ADDED | COMMENTS |
| II | 84.79 | 11.08 | 0.00 | 0.57 | 1.6 HRS | 12.0 | 0.6 g. 5% Pd/C | 48 g. MeOH | 227 | 45° C., white crystals |
| III | 74.11 | 0.33 | 0.00 | 16.00 | 1.1 HRS | 18.0 | 1.3 g. 5% Pd/C | 42 g. MeOH | 323 | 55° C., white crystals |
| IV | 83.33 | 0.00 | 0.00 | 10.60 | 3.2 HRS | 6.0 | 0.2 g. 5% Pd/C | 54 g. MeOH | 108 | 35° C., white crystals |
| V | 35.97 | 48.96 | 5.97 | 2.46 | 2.0 HRS | 6.9 | 0.6 g. 5% Pd/C | 51 g. EtOH | 270 | 35° C., RXN PSI 300, white crystal |
| VI | 47.30 | 41.48 | 5.22 | 2.64 | 1.0 HRS | 6.0 | 0.6 g. 5% Pd/C | 51 g. EtOH | **** | 35° C., RXN PSI 300, white crystal |
| VII | 78.95 | 0.00 | 0.00 | 16.57 | 3.0 HRS | 6.0 | 0.6 g. 5% Pd/C | 50 g. MeOH | **** | 35° C., RXN PSI 300, white crystal |
| VIII | | | | | 2.5 HRS | 6.0 | 0.6 g. 5% Pd/C | 45.5 g. MeOH/ 5.6 g. $H_2O$ | 740 | 81° C., RXN PSI 300, liquid after rotovap |
| IX | 86.90 | 0.00 | *** | 10.11 | 2.0 HRS | 8.0 | 0.4 g. 5% Pd/C | 53.4 g. MeOH | 780 | 35° C., RXN PSI 300, white crystal |
| X | 81.36 | 0.86 | *** | 3.55 | 2.0 HRS | 8.0 | 0.2 g. 5% Pd/C | 53.4 g. MeOH | 530 | 35° C., RXN PSI 300, white crystal |
| XI | 28.52 | 69.22 | *** | 2.26 | 4.0 HRS | 20.0 | 1.0 g. 5% Pd/C | 40 g. MeOH | 390 | 35° C., RXN PSI 300, white crystal |
| XII | | | | | 4.5 HRS | 20.0 | 1.0 g. 5% Pd/C | 39.9 g. MeOH | 1140 | 35° C., RXN PSI 300, white crystal |

EXAMPLES XIII–XVIII

Example XIII—A 500 ml three neck flask was fitted with a dean stark trap with condenser, mechanical stirrer, and a nitrogen inlet. To the flask was added 4-hydroxyphenylmethylcarbinol-HPMC (34.14 g, 0.25 moles) and the flask was thoroughly purged with nitrogen. The solid was heated to 150° C. with an oil bath for 15 hours. During this time, the solid became a melt and water was released. The melt solidified upon cooling to room temperature, and the solid was dissolved in methanol (100 g). The solution was precipitated into water (800 ml) and the solid was isolated by filtration, washed with water (100 ml), dried (25° C., 100 torr), and weighed (26.0 g, 0.22 moles, 87%). The poly(hydroxystyrene) obtained was soluble in polar organic solvents such as acetone, methanol, tetrahydrofuran, etc. The $\bar{M}_m$ was 2025 and the $\bar{M}_n$ was 1328, and the $\bar{M}_m/\bar{M}_n$ was 1.53 respectively.

Example XIV—The same procedure as in Example XIII except phosphoric acid (0.13 g) was used as a dehydration and polymerization catalyst, with 4-hydroxyphenylmethylcarbinol (32 g, 0.23 moles) and the reaction time was twenty hours. The polymer was isolated in a similar manner giving a yield of 81%, a $\bar{M}_m$ of 3324, a $\bar{M}_n$ of 1819, and a $\bar{M}_m/\bar{M}_n$ of 1.83.

Example XV—The same procedure as in Example XIV except VA-086 (2,2'-azobis[2-methyl-N-( 2-hydroxyethyl-)propionamide], Wako Chemicals) (0.13 g) was used as a radical initiator, with 4-hydroxyphenylmethylcarbinol (32.3 g, 0.24 moles) with a reaction time of 22.5 hours. The polymer was isolated in a similar manner giving a yield of 85%, a $\bar{M}_m$ of 2255, a $\bar{M}_n$ of 1420, and a $\bar{M}_m/\bar{M}_n$ of 1.59.

Example XVI—To a 100 cc autoclave, 4-hydroxyphenylmethylcarbinol (4.4 g, 0.03 moles) and water (17.6 g) were added. The reactor was thoroughly purged with nitrogen. The mixture was heated to 150° C. for 16 hours. The maximum pressure attained during this time was 170 psi. The reactor was cooled to 40° C. and the reactor was vented and purged with nitrogen. The liquid layer was decanted and the remaining solid was dissolved in methanol (11.7 g). The solution was then precipitated into water (150 ml). The solid was isolated by filtration and washed with water (100 ml), dried (25° C., 100 torr), and weighed (3.28 g, 0.03 moles, 85%). The poly(hydroxystyrene) obtained was soluble in polar organic solvents such as acetone, methanol, tetrahydrofuran, etc. The $\bar{M}_m$ was 2412 and the $\bar{M}_n$ was 1443, and the $\bar{M}_m/\bar{M}_n$ was 1.67 respectively.

Example XVII—The same procedure as in Example XVI except polyacrylic acid (1.0 g, 25% PAA in water) was used as a suspension aid and catalyst, with 4-hydroxyphenylmethylcarbinol (9.98 g, 0.07 moles), and water (30.6 g), and the reaction time was 15.5 hours. The maximum pressure attained during this time was 175 psi. The polymer was isolated in a similar manner giving a yield of 78%, a $\bar{M}_m$ of 4520, a $\bar{M}_n$ of 2428, and a $\bar{M}_m/\bar{M}_n$ of 1.86.

Example XVIII—The same procedure as in Example XIII except stearic acid (1.0 g) was used as a suspension aid with HPMC (20.4 g, 0.15 moles) and water (60.9 g). The polymer was isolated in a similar manner giving a yield of 81%, a $\bar{M}_m$ of 1224, a $\bar{M}_n$ of 817, and a $\bar{M}_m/\bar{M}_n$ of 1.50.

While the above has been described using 4-hydroxyacetophenone (4-HAP) as the starting material, it is also within the scope of the present invention to use (1) other hydroxyacetophenones (wherein the hydroxy substituents are positioned at different locations on the phenyl ring), and (2) substituted hydroxyacetophenones wherein the remaining four hydrogen atoms (on the phenyl ring) are selectively replaced by an R group, said R being selected from the group consisting of (a) $C_1$–$C_8$ alkyl; (b) $C_6H_5$; (c) halogen (F, Cl, Br, I); (d) hydroxy; and (e) OR where R is the same as defined above. These hydroxyacetophenones and substituted hydroxyacetophenones are all suitable starting materials for use in the present invention process.

Although the invention has been illustrated by the preceding examples, it is not to be construed s being limited thereby; but rather, the invention encompasses the generic area as hereinbefore disclosed. Various modifications and embodiments can be made without departing from the spirit and scope thereof.

What is claimed is:

1. A process for preparing polyhydroxystyrene which comprises the steps of (a) heating 4-hydroxyacetophenone under suitable hydrogenation conditions of temperature and pressure in the presence of a suitable palladium catalyst and for a sufficient period of time to form 4-hydroxyphenylmethylcarbinol; (b) heating 4-hydroxyphenylmethylcarbinol under suitable conditions of temperature and pressure and for a sufficient period of time to form said polyhydroxystyrene.

2. The process as set forth in claim 1 wherein in step (a) the temperature is at least about 20° C.

3. The process as set forth in claim 1 wherein in step (a) the reaction takes place in the presence of an organic solvent.

4. The process as set forth in claim 1 wherein in step (a) the reaction takes place in the presence of water.

5. The process as set forth in claim 1 wherein in step (a) the temperature is from about 20° C. to about 100° C.

6. The process as set forth in claim 1 wherein the palladium catalyst is selected from the group consisting of Pd/C; Pd/$Al_2O_3$; Pd/$SiO_2$; and Pd/$CaCO_3$.

7. The process as set forth in claim 1 wherein such heating is conducted in the presence of a catalyst which is Pd/C.

8. The process as set forth in claim 3 wherein in step (a), such heating is conducted in the presence of a catalyst which is Pd/C.

9. The process as set forth in claim 1 wherein in step (b), the temperature is at least about 70° C.

10. The process as set forth in claim 1 wherein in step (b), the reaction takes place in the presence of an organic solvent.

11. The process as set forth in claim 1 wherein in step (b), the reaction takes place in the presence of water.

12. The process as set forth in claim 1 wherein in step (b), the reaction takes place in the presence of a solvent which is a mixture of an organic solvent and water.

13. The process as set forth in claim 1 wherein in step (b), the reaction takes place in the presence of an accelerator.

14. The process as set forth in claim 6 wherein in step (b), the reaction takes place in the presence of a catalyst.

15. The process as set forth in claim 7 wherein in step (b), the reaction takes place in the presence of a suspension aid.

16. The process as set forth in claim 11 wherein the amount of water present is 1% to 300% by weight, based on the amount of 4-hydroxyphenylmethylcarbinol.

17. A process as set forth in claim 13 wherein the polymerization accelerator is selected from the group consisting of at least one cationic initiator selected from inorganic acids, metal halides, complexes of boron trifluoride, aliphatic saturated monocarboxylic acids, aliphatic saturated polycarboxylic acids, aliphatic unsaturated monocarboxylic acids, aliphatic unsaturated polycarboxylic acids, aromatic carboxylic acids, and organic sulfonic acids.

18. A process as set forth in claim 13 wherein the polymerization accelerator is selected from the group consisting of at least one radical initiator selected from azoisobutyronitrile, benzoyl peroxide, and ammonium persulfate.

19. A process as set forth in claim 18 wherein the amount of the polymerization accelerator present is from about 0.005 to about 10% by weight based on the amount of 4-hydroxyphenylmethylcarbinol.

20. A process as set forth in claim 19 wherein the polymerization reaction temperature is from about 70° C. to about 300° C.

21. The process as set forth in claim 1 wherein in step (b), there are two phases, including a first phase, wherein said carbinol is heated under decomposition conditions to dehydrate said carbinol to form 4-hydroxystyrene; and a second phase wherein said 4-hydroxystyrene is heated under suitable polymerization conditions of pressure and temperature and for a sufficient period of time to form poly(4-hydroxystryrene).

* * * * *